United States Patent
Malandain (10) Patent No.: US 8,114,135 B2
(45) Date of Patent: Feb. 14, 2012

(54) ADJUSTABLE SURGICAL CABLES AND METHODS FOR TREATING SPINAL STENOSIS

(75) Inventor: Hugues F. Malandain, Mountain View, CA (US)

(73) Assignee: Kyphon Sarl, Neuchatel (CH)

( * ) Notice: Subject to any disclaimer, the term of this patent is extended or adjusted under 35 U.S.C. 154(b) by 492 days.

(21) Appl. No.: 12/355,065

(22) Filed: Jan. 16, 2009

(65) Prior Publication Data

US 2010/0185241 A1    Jul. 22, 2010

(51) Int. Cl.
*A61B 17/70* (2006.01)

(52) U.S. Cl. ......... 606/263; 606/151; 606/279; 128/896

(58) Field of Classification Search .................. 606/246, 606/57, 105, 258, 263, 279; 623/17.11–17.16, 623/13.13; 411/250, 530
See application file for complete search history.

(56) References Cited

U.S. PATENT DOCUMENTS

| | | | |
|---|---|---|---|
| 278,097 A | 5/1883 | Collins | |
| 1,706,431 A | 3/1929 | Whitliff | |
| 2,502,902 A | 4/1950 | Tofflemire | |
| 2,677,369 A | 5/1954 | Knowles | |
| 3,648,691 A | 3/1972 | Lumb et al. | |
| 3,654,668 A | 4/1972 | Appleton | |
| 3,678,542 A | 7/1972 | Prete, Jr. | |
| 4,003,376 A | 1/1977 | McKay et al. | |
| 4,011,602 A | 3/1977 | Rybicki et al. | |
| 4,047,523 A | 9/1977 | Hall | |
| 4,257,409 A | 3/1981 | Bacal et al. | |
| 4,448,191 A | 5/1984 | Rodnyansky et al. | |
| 4,554,914 A | 11/1985 | Kapp et al. | |
| 4,570,618 A | 2/1986 | Wu | |
| 4,573,454 A | 3/1986 | Hoffman | |
| 4,604,995 A | 8/1986 | Stephens et al. | |
| 4,643,174 A | 2/1987 | Horiuchi | |
| 4,643,178 A | 2/1987 | Nastari et al. | |
| 4,686,970 A | 8/1987 | Dove et al. | |
| 4,776,851 A | 10/1988 | Bruchman et al. | |
| 4,779,816 A | 10/1988 | Varlet | |

(Continued)

FOREIGN PATENT DOCUMENTS

DE  2821678 A1  11/1979

(Continued)

OTHER PUBLICATIONS

"Dispositivo Intervertebrale Ammortizzante DIAM," date unknown, p. 1.

(Continued)

*Primary Examiner* — Eduardo C Robert
*Assistant Examiner* — Christina Negrelli (57) ABSTRACT

An apparatus includes a surgical cable, a coupling member and an adjustment mechanism. The surgical cable has a first end portion and a second end portion. The coupling member is coupled to the first end portion of the surgical cable, and defines an opening therethrough. The adjustment mechanism includes a housing and an elongate member. The housing defines a first opening and a second opening. A portion of a side wall of the housing defines a threaded portion within the second opening. The elongate member has an end portion and a threaded portion. The end portion of the elongate member is coupled to the second end portion of the surgical cable. The threaded portion of the elongate member is disposed within the second opening of the housing such that the threaded portion of the elongate member is engaged with the threaded portion of the second opening.

22 Claims, 6 Drawing Sheets

U.S. PATENT DOCUMENTS

| | | | |
|---|---|---|---|
| 4,827,918 A | 5/1989 | Olerud | |
| 4,841,959 A | 6/1989 | Ransford | |
| 4,998,936 A | 3/1991 | Mehdian | |
| 5,000,165 A | 3/1991 | Watanabe | |
| 5,011,484 A | 4/1991 | Breard | |
| 5,030,220 A | 7/1991 | Howland | |
| 5,047,055 A | 9/1991 | Bao et al. | |
| 5,092,866 A | 3/1992 | Breard et al. | |
| 5,133,717 A | 7/1992 | Chopin | |
| 5,180,393 A | 1/1993 | Commarmond | |
| 5,201,734 A | 4/1993 | Cozad et al. | |
| 5,306,275 A | 4/1994 | Bryan | |
| 5,356,412 A | 10/1994 | Golds et al. | |
| 5,356,417 A | 10/1994 | Golds | |
| 5,360,430 A | 11/1994 | Lin | |
| 5,366,455 A | 11/1994 | Dove | |
| 5,395,374 A * | 3/1995 | Miller et al. | 606/74 |
| 5,415,659 A | 5/1995 | Lee et al. | |
| 5,415,661 A | 5/1995 | Holmes | |
| 5,437,672 A | 8/1995 | Alleyne | |
| 5,454,812 A | 10/1995 | Lin | |
| 5,496,318 A | 3/1996 | Howland et al. | |
| 5,575,819 A | 11/1996 | Amis | |
| 5,609,634 A | 3/1997 | Voydeville | |
| 5,628,756 A | 5/1997 | Barker, Jr. et al. | |
| 5,645,599 A | 7/1997 | Samani | |
| 5,674,295 A | 10/1997 | Ray et al. | |
| 5,676,702 A | 10/1997 | Ratron | |
| 5,690,649 A | 11/1997 | Li | |
| 5,702,452 A | 12/1997 | Argenson et al. | |
| 5,725,582 A | 3/1998 | Bevan et al. | |
| 5,782,831 A | 7/1998 | Sherman et al. | |
| 5,810,815 A | 9/1998 | Morales | |
| 5,836,948 A | 11/1998 | Zucherman et al. | |
| 5,860,977 A | 1/1999 | Zucherman et al. | |
| 5,976,186 A | 11/1999 | Bao et al. | |
| 6,022,376 A | 2/2000 | Assell et al. | |
| 6,048,342 A | 4/2000 | Zucherman et al. | |
| 6,068,630 A | 5/2000 | Zucherman et al. | |
| 6,090,043 A | 7/2000 | Austin et al. | |
| 6,132,464 A | 10/2000 | Martin | |
| 6,293,949 B1 | 9/2001 | Justis et al. | |
| 6,312,431 B1 | 11/2001 | Asfora | |
| 6,352,537 B1 | 3/2002 | Strnad | |
| 6,364,883 B1 | 4/2002 | Santilli | |
| 6,368,326 B1 | 4/2002 | Dakin et al. | |
| 6,402,750 B1 | 6/2002 | Atkinson et al. | |
| 6,440,169 B1 | 8/2002 | Elberg et al. | |
| 6,451,019 B1 | 9/2002 | Zucherman et al. | |
| 6,520,990 B1 | 2/2003 | Ray | |
| 6,582,433 B2 | 6/2003 | Yun | |
| 6,605,091 B1 | 8/2003 | Iwanski | |
| 6,626,944 B1 | 9/2003 | Taylor | |
| 6,641,584 B2 | 11/2003 | Hashimoto et al. | |
| 6,645,207 B2 | 11/2003 | Dixon et al. | |
| 6,695,842 B2 | 2/2004 | Zucherman et al. | |
| 6,709,435 B2 | 3/2004 | Lin | |
| 6,723,126 B1 | 4/2004 | Berry | |
| 6,733,534 B2 | 5/2004 | Sherman | |
| 6,761,720 B1 | 7/2004 | Senegas | |
| 6,835,205 B2 | 12/2004 | Atkinson et al. | |
| 6,946,000 B2 | 9/2005 | Senegas et al. | |
| 7,041,136 B2 | 5/2006 | Goble et al. | |
| 7,048,736 B2 | 5/2006 | Robinson et al. | |
| 7,087,083 B2 | 8/2006 | Pasquet et al. | |
| 7,101,375 B2 | 9/2006 | Zucherman et al. | |
| 7,163,558 B2 | 1/2007 | Senegas et al. | |
| 7,201,751 B2 | 4/2007 | Zucherman et al. | |
| 7,238,204 B2 | 7/2007 | Le Couedic et al. | |
| 7,306,628 B2 | 12/2007 | Zucherman et al. | |
| 7,335,203 B2 | 2/2008 | Winslow et al. | |
| 7,367,978 B2 * | 5/2008 | Drewry et al. | 606/279 |
| 7,377,942 B2 | 5/2008 | Berry | |
| 7,442,208 B2 | 10/2008 | Mathieu et al. | |
| 7,445,637 B2 | 11/2008 | Taylor | |
| 7,458,981 B2 | 12/2008 | Fielding et al. | |
| 7,524,324 B2 | 4/2009 | Winslow et al. | |
| 7,842,072 B2 * | 11/2010 | Dawson | 606/263 |
| 2002/0143331 A1 | 10/2002 | Zucherman et al. | |
| 2002/0188297 A1 * | 12/2002 | Dakin et al. | 606/72 |
| 2003/0040746 A1 | 2/2003 | Mitchell et al. | |
| 2003/0065330 A1 | 4/2003 | Zucherman et al. | |
| 2003/0153915 A1 | 8/2003 | Nekozuka et al. | |
| 2004/0097931 A1 | 5/2004 | Mitchell | |
| 2004/0127907 A1 * | 7/2004 | Dakin et al. | 606/72 |
| 2005/0010293 A1 | 1/2005 | Zucherman et al. | |
| 2005/0049708 A1 | 3/2005 | Atkinson et al. | |
| 2005/0165398 A1 | 7/2005 | Reiley | |
| 2005/0203512 A1 | 9/2005 | Hawkins et al. | |
| 2005/0203624 A1 | 9/2005 | Serhan et al. | |
| 2005/0209603 A1 | 9/2005 | Zucherman et al. | |
| 2005/0228391 A1 | 10/2005 | Levy et al. | |
| 2005/0261768 A1 | 11/2005 | Trieu | |
| 2005/0288672 A1 | 12/2005 | Feree | |
| 2006/0004447 A1 | 1/2006 | Mastrorio et al. | |
| 2006/0015181 A1 | 1/2006 | Elberg | |
| 2006/0036246 A1 | 2/2006 | Carl et al. | |
| 2006/0047282 A1 * | 3/2006 | Gordon | 606/61 |
| 2006/0064165 A1 | 3/2006 | Zucherman et al. | |
| 2006/0084983 A1 | 4/2006 | Kim | |
| 2006/0084985 A1 | 4/2006 | Kim | |
| 2006/0084987 A1 | 4/2006 | Kim | |
| 2006/0084988 A1 | 4/2006 | Kim | |
| 2006/0085069 A1 | 4/2006 | Kim | |
| 2006/0085070 A1 | 4/2006 | Kim | |
| 2006/0085074 A1 | 4/2006 | Raiszadeh | |
| 2006/0089654 A1 | 4/2006 | Lins et al. | |
| 2006/0089719 A1 | 4/2006 | Trieu | |
| 2006/0106381 A1 | 5/2006 | Ferree et al. | |
| 2006/0106397 A1 | 5/2006 | Lins | |
| 2006/0111728 A1 | 5/2006 | Abdou | |
| 2006/0122620 A1 | 6/2006 | Kim | |
| 2006/0136060 A1 | 6/2006 | Taylor | |
| 2006/0149278 A1 | 7/2006 | Abdou | |
| 2006/0184247 A1 | 8/2006 | Edidin et al. | |
| 2006/0184248 A1 | 8/2006 | Edidin et al. | |
| 2006/0195102 A1 | 8/2006 | Malandain | |
| 2006/0217726 A1 | 9/2006 | Maxy et al. | |
| 2006/0224159 A1 | 10/2006 | Anderson | |
| 2006/0235386 A1 | 10/2006 | Anderson | |
| 2006/0235387 A1 | 10/2006 | Peterman | |
| 2006/0235532 A1 | 10/2006 | Meunier et al. | |
| 2006/0241601 A1 | 10/2006 | Trautwein et al. | |
| 2006/0241610 A1 | 10/2006 | Lim et al. | |
| 2006/0241613 A1 | 10/2006 | Bruneau et al. | |
| 2006/0241614 A1 | 10/2006 | Bruneau et al. | |
| 2006/0241757 A1 | 10/2006 | Anderson | |
| 2006/0247623 A1 | 11/2006 | Anderson et al. | |
| 2006/0247640 A1 | 11/2006 | Blackwell et al. | |
| 2006/0264938 A1 | 11/2006 | Zucherman et al. | |
| 2006/0271044 A1 | 11/2006 | Petrini et al. | |
| 2006/0271049 A1 | 11/2006 | Zucherman et al. | |
| 2006/0293662 A1 | 12/2006 | Boyer et al. | |
| 2006/0293663 A1 | 12/2006 | Walkenhorst et al. | |
| 2007/0005064 A1 | 1/2007 | Anderson et al. | |
| 2007/0043362 A1 | 2/2007 | Malandain et al. | |
| 2007/0100340 A1 | 5/2007 | Lange et al. | |
| 2007/0123861 A1 | 5/2007 | Dewey et al. | |
| 2007/0162000 A1 | 7/2007 | Perkins | |
| 2007/0167945 A1 | 7/2007 | Lange et al. | |
| 2007/0173822 A1 | 7/2007 | Bruneau et al. | |
| 2007/0173823 A1 | 7/2007 | Dewey et al. | |
| 2007/0191833 A1 | 8/2007 | Bruneau et al. | |
| 2007/0191834 A1 | 8/2007 | Bruneau et al. | |
| 2007/0191837 A1 | 8/2007 | Trieu | |
| 2007/0191838 A1 | 8/2007 | Bruneau et al. | |
| 2007/0198091 A1 | 8/2007 | Boyer et al. | |
| 2007/0233068 A1 | 10/2007 | Bruneau et al. | |
| 2007/0233074 A1 | 10/2007 | Anderson et al. | |
| 2007/0233076 A1 | 10/2007 | Trieu | |
| 2007/0233081 A1 | 10/2007 | Pasquet et al. | |
| 2007/0233089 A1 | 10/2007 | DiPoto et al. | |
| 2007/0250060 A1 | 10/2007 | Anderson et al. | |
| 2007/0270823 A1 | 11/2007 | Trieu et al. | |
| 2007/0270824 A1 | 11/2007 | Lim et al. | |
| 2007/0270825 A1 | 11/2007 | Carls et al. | |
| 2007/0270826 A1 | 11/2007 | Trieu et al. | |

| 2007/0270827 A1 | 11/2007 | Lim et al. |
| 2007/0270828 A1 | 11/2007 | Bruneau et al. |
| 2007/0270829 A1 | 11/2007 | Carls et al. |
| 2007/0270834 A1 | 11/2007 | Bruneau et al. |
| 2007/0270874 A1 | 11/2007 | Anderson |
| 2007/0272259 A1 | 11/2007 | Allard et al. |
| 2007/0276368 A1 | 11/2007 | Trieu et al. |
| 2007/0276369 A1 | 11/2007 | Allard et al. |
| 2007/0276496 A1 | 11/2007 | Lange et al. |
| 2007/0276497 A1 | 11/2007 | Anderson |
| 2008/0009866 A1 | 1/2008 | Alamin et al. |
| 2008/0015693 A1 | 1/2008 | Le Couedic |
| 2008/0021460 A1 | 1/2008 | Bruneau et al. |
| 2008/0114357 A1 | 5/2008 | Allard et al. |
| 2008/0114358 A1 | 5/2008 | Anderson et al. |
| 2008/0114456 A1 | 5/2008 | Dewey et al. |
| 2008/0140082 A1 | 6/2008 | Erdem et al. |
| 2008/0147190 A1 | 6/2008 | Dewey et al. |
| 2008/0161818 A1 | 7/2008 | Kloss et al. |
| 2008/0167685 A1 | 7/2008 | Allard et al. |
| 2008/0183211 A1 | 7/2008 | Lamborne et al. |
| 2008/0281360 A1 | 11/2008 | Vittur et al. |
| 2008/0281361 A1 | 11/2008 | Vittur et al. |
| 2009/0062915 A1 | 3/2009 | Kohm et al. |
| 2009/0099610 A1* | 4/2009 | Johnson et al. ............. 606/86 R |
| 2009/0105773 A1 | 4/2009 | Lange et al. |
| 2009/0270918 A1 | 10/2009 | Attia et al. |

FOREIGN PATENT DOCUMENTS

| EP | 0322334 B1 | 2/1992 |
| EP | 2799948 A1 | 4/2001 |
| EP | 1138268 A1 | 10/2001 |
| EP | 1330987 A1 | 7/2003 |
| FR | 2623085 A1 | 5/1989 |
| FR | 2625097 A1 | 6/1989 |
| FR | 2681525 A1 | 3/1993 |
| FR | 2700941 A1 | 8/1994 |
| FR | 2703239 A1 | 10/1994 |
| FR | 2707864 A1 | 1/1995 |
| FR | 2717675 A1 | 9/1995 |
| FR | 2722087 A1 | 1/1996 |
| FR | 2722088 A1 | 1/1996 |
| FR | 2724554 A1 | 3/1996 |
| FR | 2725892 A1 | 4/1996 |
| FR | 2730156 A1 | 8/1996 |
| FR | 2775183 A1 | 8/1999 |
| FR | 2816197 A1 | 5/2002 |
| FR | 2884135 A1 | 4/2005 |
| JP | 02-224660 | 9/1990 |
| JP | 09-075381 | 3/1997 |
| SU | 988281 | 1/1983 |
| SU | 1484348 A1 | 6/1989 |
| WO | WO 94/26192 | 11/1994 |
| WO | WO 94/26195 | 11/1994 |
| WO | WO 98/20939 | 5/1998 |
| WO | WO 2004/047691 A1 | 6/2004 |
| WO | WO 2005/009300 A1 | 2/2005 |
| WO | WO 2005/037150 A1 | 4/2005 |
| WO | WO 2005/044118 A1 | 5/2005 |
| WO | WO 2005/110258 A1 | 11/2005 |
| WO | WO 2006/064356 A1 | 6/2006 |
| WO | WO 2006/110578 A2 | 10/2006 |
| WO | WO 2007/034516 A1 | 3/2007 |

OTHER PUBLICATIONS

"Tecnica Operatoria Per Il Posizionamento Della Protesi DIAM," date unknown, pp. 1-3.

"Wallis Operative Technique: Surgical Procedure for Treatment of Degenerative Disc Disease (DDD) of Lumbar Spine," date unknown, pp. 1-24, Spine Next, an Abbott Laboratories company, Bordeaux, France.

Aota et al., "Postfusion Instability at the Adjacent Segments After Rigid Pedicle Screw Fixation for Degenerative Lumbar Spinal Disorders," J. Spinal Dis., Dec. 1995, pp. 464-473, vol. 8, No. 6.

Benzel et al., "Posterior Cervical Interspinous Compression Wiring and Fusion for Mid to Low Cervical Spinal Injuries," J. Neurosurg., Jun. 1989, pp. 893-899, vol. 70.

Booth et al., "Complications and Predictive Factors for the Successful Treatment of Flatback Deformity (Fixed Sagittal Imbalance)," SPINE, 1999, pp. 1712-1720, vol. 24, No. 16.

Caserta et al., "Elastic Stabilization Alone or Combined with Rigid Fusion in Spinal Surgery: a Biomechanical Study and Clinical Experience Based on 82 Cases," Eur. Spine J., Oct. 2002, pp. S192- S197, vol. 11, Suppl. 2.

Christie et al., "Dynamic Interspinous Process Technology," SPINE, 2005, pp. S73-S78, vol. 30, No. 16S.

Cousin Biotech, "Analysis of Clinical Experience with a Posterior Shock-Absorbing Implant," date unknown, pp. 2-9.

Cousin Biotech, Dispositif Intervertebral Amortissant, Jun. 1998, pp. 1-4.

Cousin Biotech, Technique Operatoire de la Prothese DIAM, date unknown, Annexe 1, pp. 1-8.

Dickman et al., "The Interspinous Method of Posterior Atlantoaxial Arthrodesis," J. Neurosurg., Feb. 1991, pp. 190-198, vol. 74.

Dubois et al., "Dynamic Neutralization: A New Concept for Restabilization of the Spine," Lumbar Segmental Insability, Szpalski et al., eds., 1999, pp. 233-240, Lippincott Williams & Wilkins, Philadelphia, Pennsylvania.

Ebara et al., "Inoperative Measurement of Lumbar Spinal Instability," SPINE, 1992, pp. S44-S50, vol. 17, No. 3S.

Fassio et al., "Treatment of Degenerative Lumbar Spinal Instability L4-L5 by Interspinous Ligamentoplasty," Rachis, Dec. 1991, pp. 465-474, vol. 3, No. 6.

Fassio, "Mise au Point Sur la Ligamentoplastie Inter-Epineuse Lombaire Dans les Instabilites," Maitrise Orthopedique, Jul. 1993, pp. 18, No. 25.

Garner et al., "Development and Preclinical Testing of a New Tension-Band Device for the Spine: the Loop System," Eur. Spine J., Aug. 7, 2002, pp. S186-S191, vol. 11, Suppl. 2.

Guang et al., "Interspinous Process Segmental Instrumentation with Bone-Button-Wire for Correction of Scoliosis," Chinese Medical J., 1990, pp. 721-725, vol. 103.

Guizzardi et al., "The Use of DIAM (Interspinous Stress-Breaker Device) in the Prevention of Chronic Low Back Pain in Young Patients Operated on for Large Dimension Lumbar Disc Herniation," 12th Eur. Cong. Neurosurg., Sep. 7-12, 2003, pp. 835-839, Port.

Hambly et al., "Tension Band Wiring-Bone Grafting for Spondylolysis and Spondylolisthesis," SPINE, 1989, pp. 455-460, vol. 14, No. 4.

Kiwerski, "Rehabilitation of Patients with Thoracic Spine Injury Treated by Spring Alloplasty," Int. J. Rehab. Research, 1983, pp. 469-474, vol. 6, No. 4.

Laudet et al., "Comportement Bio-Mécanique D'Un Ressort Inter-Apophysaire Vertébral Postérieur Analyse Expérimentale Due Comportement Discal En Compression Et En Flexion/Extension," Rachis, 1993, vol. 5, No. 2.

Mah et al., "Threaded K-Wire Spinous Process Fixation of the Axis for Modified Gallie Fusion in Children and Adolescents," J. Pediatric Othopaedics, 1989, pp. 675-679, vol. 9.

Mariottini et al., "Preliminary Results of a Soft Novel Lumbar Intervertebral Prothesis (DIAM) in the Degenerative Spinal Pathology," Acta Neurochir., Adv. Peripheral Nerve Surg. and Minimal Invas. Spinal Surg., 2005, pp. 129-131, vol. 92, Suppl.

McDonnell et al., "Posterior Atlantoaxial Fusion: Indications and Techniques," Techniques in Spinal Fusion and Stabilization, Hitchon et al., eds., 1995, pp. 92-106, Ch. 9, Thieme, New York.

Minns et al., "Preliminary Design and Experimental Studies of a Novel Soft Implant for Correcting Sagittal Plane Instability in the Lumbar Spine," SPINE, 1997, pp. 1819-1825, vol. 22, No. 16.

Müller, "Restauration Dynamique de la Stabilité Rachidienne," Tiré de la Sulzer Technical Review, Jan. 1999, Sulzer Management Ltd, Winterthur, Switzerland.

Pennal et al., "Stenosis of the Lumbar Spinal Canal," Clinical Neurosurgery: Proceedings of the Congress of Neurological Surgeons, St. Louis, Missouri, 1970, Tindall et al., eds., 1971, Ch. 6, pp. 86-105, vol. 18.

Petrini et al., "Analisi Di Un'Esperienza Clinica Con Un Impianto Posteriore Ammortizzante," S.O.T.I.M.I. Societè di Ortopedia e Traumatologia dell'Italia Meridionale e Insulare 90 ° Congresso, Jun. 21-23, 2001, Paestum.

Petrini et al., "Stabilizzazione Elastica," Patologia Degenerative del Rachide Lombare, Oct. 5-6, 2001, Rimini.

Porter, "Spinal Stenosis and Neurogenic Claudication," SPINE, Sep. 1, 1996, pp. 2046-2052, vol. 21, No. 17.

Pupin et al., "Clinical Experience with a Posterior Shock-Absorbing Implant in Lumbar Spine," World Spine 1: First Interdisciplinary World Congress on Spinal Surgery and Related Disciplines, Aug. 27-Sep. 1, 2000, Berlin, Germany.

Rahm et al., "Adjacent-Segment Degeneration After Lumbar Fusion with Instrumentation: A Retrospective Study," J. Spinal Dis., Oct. 1996, pp. 392-400, vol. 9, No. 5.

Rengachary et al., "Cervical Spine Stabilization with Flexible, Multistrand Cable System," Techniques in Spinal Fusion and Stabilization, Hitchon et al., eds., 1995, pp. 79-81, Ch. 7, Thieme, New York.

Richards et al., "The Treatment Mechanism of an Interspinous Process Implant for Lumbar Neurogenic Intermittent Claudication," SPINE, 2005, pp. 744-749, vol. 30, No. 7.

Scarfò, "Instability/Stenosis: Holistic Approach for Less Invasive Surgery," date unknown, University of Siena, Siena, Italy.

Schären et al, "Erfolge and Probleme langstreckiger Fusionen der degenerativen Lendenwirbelsäule," Osteosynthese International, Jul. 17, 1998, pp. 173-179, vol. 6, Johann Ambrosius Barth.

Schiavone et al., "The Use of Disc Assistance Prosthesis (DIAM) in Degenerative Lumbar Pathology: Indications, Technique, Results," Italian J. Spinal Disorders, 2003, pp. 213-220, vol. 3, No. 2.

Schlegel et al., "Lumbar Motion Segment Pathology Adjacent to Thoracolumbar, Lumbar, and Lumbosacral Fusions," SPINE, Apr. 15, 1996, pp. 970-981, vol. 21, No. 8.

Schlegel et al., "The Role of Distraction in Improving the Space Available in the Lumbar Stenotic Canal and Foramen," SPINE, 1994, pp. 2041-2047, vol. 19, No. 18.

Senegas et al., "Le Recalibrage du Canal Lombaire, Alternative à la Laminectomie dans le Traitement des Sténoses du Canal Lombaire," Revue de Chirurgie Orthopédique, 1988, pp. 15-22.

Senegas et al., "Stabilisation Lombaire Souple," Instabilité Vertébrales Lombaires, Gastambide, ed., 1995, pp. 122-132, Expansion Scientifique Française, Paris, France.

Senegas, "La Ligamentoplastie Inter Vertébrale Lombaire, Alternative a L'Arthrodèse," La Revue de Medécine Orthopédique, Jun. 1990, pp. 33-35, No. 20.

Senegas, "La Ligamentoplastie Intervertébrale, Alternative à L'arthrodèse dans le Traitement des Instabilités Dégénératives," Acta Othopaedica Belgica, 1991, pp. 221-226, vol. 57, Suppl. I.

Senegas, "Mechanical Supplementation by Non-Rigid Fixation in Degenerative Intervertebral Lumbar Segments: the Wallis System," Eur. Spine J., 2002, p. S164-S169, vol. 11, Suppl. 2.

Senegas, "Rencontre," Maîtrise Orthopedique, May 1995, pp. 1-3, No. 44.

Serhan, "Spinal Implants: Past, Present, and Future," 19th International IEEE/EMBS Conference, Oct. 30-Nov. 2, 1997, pp. 2636-2639, Chicago, Illinois.

Spadea et al., "Interspinous Fusion for the Treatment of Herniated Intervertebral Discs: Utilizing a Lumbar Spinous Process as a Bone Graft," Annals of Surgery, 1952, pp. 982-986, vol. 136, No. 6.

Sulzer Innotec, "DIAM—Modified CAD Geometry and Meshing," date unknown.

Taylor et al., "Analyse d'une expérience clinique d'un implant postérieur amortissant," Rachis Revue de Pathologie Vertébrale, Oct./Nov. 1999, vol. 11, No. 4-5, Gieda Inter Rachis.

Taylor et al., "Surgical Requirement for the Posterior Control of the Rotational Centers," date unknown.

Taylor et al., "Technical and Anatomical Considerations for the Placement of a Posterior Interspinous Stabilizer," 2004, pp. 1-10, Medtronic Sofamor Danek USA, Inc., Memphis, Tennessee.

Taylor, "Biomechanical Requirements for the Posterior Control of the Centers of Rotation," Swiss Spine Institute International Symposium: Progress in Spinal Fixation, Jun. 21-22, 2002, pp. 1-2, Swiss Spine Institute, Bern, Switzerland.

Taylor, "Non-Fusion Technologies of the Posterior Column: a New Posterior Shock Absorber," International Symposium on Intervertebral Disc Replacement and Non-Fusion-Technology, May 3-5, 2001, Spine Arthroplasty.

Taylor, "Posterior Dynamic Stabilization using the DIAM (Device for Intervertebral Assisted Motion)," date unknown, pp. 1-5.

Taylor, "Présentation à un an d'un dispositif amortissant d'assistance discale," 5èmes journées Avances & Controverses en pathologie rachidienne, Oct. 1-2, 1998, Faculté Libre de Medecine de Lille.

Tsuji et al., "Ceramic Interspinous Block (CISB) Assisted Anterior Interbody Fusion," J. Spinal Disorders, 1990, pp. 77-86, vol. 3, No. 1.

Vangilder, "Interspinous, Laminar, and Facet Posterior Cervical Bone Fusions," Techniques in Spinal Fusion and Stabilization, Hitchon et al., eds., 1995, pp. 135-146, Ch. 13, Thieme, New York.

Voydeville et al., "Experimental Lumbar Instability and Artificial Ligament," Eur. J. Orthop. Surg. Traumatol., Jul. 15, 2000, pp. 167-176, vol. 10.

Voydeville et al., "Lumbar Instability Treated by Intervertebral Ligamentoplasty with Smooth Wedges," Orthopedie Traumatologie, 1992, pp. 259-264, vol. 2, No. 4.

Waldemar Link, "Spinal Surgery: Instrumentation and Implants for Spinal Surgery," 1981, Link America Inc., New Jersey.

Wiltse et al., "The Treatment of Spinal Stenosis," Clinical Orthopaedics and Related Research, Urist, ed., Mar.-Apr. 1976, pp. 83-91, No. 115.

Wisneski et al., "Decompressive Surgery for Lumbar Spinal Stenosis," Seminars in Spine Surgery, Wiesel, ed., Jun. 1994, pp. 116-123, vol. 6, No. 2.

Wittenberg et al., "Flexibility and Distraction after Monosegmental and Bisegmental Lumbrosacral Fixation with Angular Stable Fixators," SPINE, 1995, pp. 1227-1232, vol. 20, No. 11.

Zucherman et al., "Clinical Efficacy of Spinal Instrumentation in Lumbar Degenerative Disc Disease," Spine, Jul. 1992, pp. 834-837, vol. 17, No. 7.

Kramer et al., "Intervetertebral Disk Diseases: Causes, Diagnosis, Treatment and Prophylaxis," pp. 244-249, Medical, 1990.

Zdeblick et al., "Two-Point Fixation of the Lumbar Spine Differential Stability in Rotation," SPINE, 1991, pp. S298-S301, vol. 16, No. 6, Supplement.

* cited by examiner

ADJUSTABLE SURGICAL CABLES AND METHODS FOR TREATING SPINAL STENOSIS

BACKGROUND

The invention relates generally to medical devices and procedures. More particularly, the invention relates to adjustable surgical cables and methods for treating spinal stenosis.

Spinal stenosis is a progressive narrowing of the spinal canal that causes compression of the spinal cord and nerve roots extending from the spinal cord. Each vertebra in the spinal column has an opening extending therethrough. The openings of the vertebrae are aligned vertically to form the spinal canal, within which the spinal cord is disposed. As the spinal canal narrows from spinal stenosis, the spinal cord and nerve roots extending from the spinal cord and between adjacent vertebrae are compressed and may become inflamed. Spinal stenosis can cause pain, weakness, numbness, burning sensations, tingling, and in particularly severe cases, may cause loss of bladder or bowel function, or paralysis.

Mild cases of spinal stenosis may be treated with rest or restricted activity, non-steroidal anti-inflammatory drugs (e.g., aspirin), corticosteroid injections (epidural steroids), and/or physical therapy. In certain instances the compression of the nerve roots may be surgically corrected (e.g., via a decompressive laminectomy) as the patient has increasing pain. In some known surgical procedures, bone and other tissue that has impinged upon the spinal canal and/or exerted pressure on the spinal cord can be removed. In other known surgical procedures, two adjacent vertebrae may be fused to prevent an area of instability, improper alignment or slippage, such as that caused by spondylolisthesis. In yet other known surgical procedures, spacers and/or surgical cables can be disposed between and/or about adjacent spinous processes to limit the movement between adjacent vertebrae.

Such known procedures, however, are not well suited to treat spinal stenosis in the L5-S1 location of the spinal column because the sacrum does not include a spinous process having sufficient area to support implants, tethers or the like. Moreover, known procedures that employ surgical cables often include wrapping the cable about a bone structure in a manner that limits both flexion and extension of the spinal column.

Thus, a need exists for improved surgical cables and methods for treating spinal stenosis. More particularly, a need exists for methods for treating spinal stenosis in the L5-S1 location.

SUMMARY

Apparatus and methods for treating spinal stenosis are described herein. In some embodiments, an apparatus includes a surgical cable, a coupling member and an adjustment mechanism. The surgical cable has a first end portion and a second end portion. The coupling member is coupled to the first end portion of the surgical cable, and defines an opening therethrough. The adjustment mechanism includes a housing and an elongate member. The housing defines a first opening and a second opening. A portion of a side wall of the housing defines a threaded portion within the second opening. The elongate member has an end portion and a threaded portion. The end portion of the elongate member is coupled to the second end portion of the surgical cable. The threaded portion of the elongate member is disposed within the second opening of the housing such that the threaded portion of the elongate member is engaged with the threaded portion of the second opening.

DETAILED DESCRIPTION

In some embodiments, an apparatus includes a surgical cable, a coupling member and an adjustment mechanism. The surgical cable has a first end portion and a second end portion. The coupling member is coupled to the first end portion of the surgical cable, and defines an opening therethrough. The opening of the coupling member can be configured, for example, to receive a portion of a bone screw. The adjustment mechanism includes a housing and an elongate member. The housing defines a first opening and a second opening. The first opening of the housing member can be configured, for example, to receive a portion of a bone screw. A portion of a side wall of the housing defines a threaded portion within the second opening. The elongate member has an end portion and a threaded portion. The end portion of the elongate member is coupled to the second end portion of the surgical cable. The threaded portion of the elongate member is disposed within the second opening of the housing such that the threaded portion of the elongate member is engaged with the threaded portion of the second opening. In some embodiments, for example, the end portion of the elongate member is coupled to the second end portion of the surgical cable such that rotation of the elongate member within the second opening of the housing causes the second end portion of the surgical cable to move in an axial direction relative to the housing.

In some embodiments, a method includes inserting a tether, such as, for example, a surgical cable into a body. A first end portion of the tether is coupled to a first portion of a bone structure. A second end portion of the tether is coupled to a second portion of the bone structure such that a central portion of the tether limits extension of a portion of a spinal column associated with the bone structure while allowing flexion of the portion of the spinal column. The bone structure can be, for example, an ilium of a spinal column, with the first portion of the ilium being disposed on a first side of a mid-line axis and the second portion of the ilium being disposed on a second side of a mid-line axis. In some embodiments, for example, the tension of the tether can be adjusted and/or maintained. In some embodiments, for example, coupling the second end portion of the tether can including applying a force to an inferior side of a spinous process.

As used in this specification, the words "proximal" and "distal" refer to the direction closer to and away from, respectively, an operator (e.g., surgeon, physician, nurse, technician, etc.) who would insert a medical device into the patient, with the tip-end (i.e., distal end) of the device inserted inside a patient's body first. Thus, for example, the end of a medical device first inserted into the patient's body is the distal end, while the opposite end of the medical device (i.e., the end of the medical device last inserted into to the patient's body and/or the end of the medical device being manipulated by the operator) is the proximal end of the medical device.

The term "parallel" is used herein to describe a relationship between two geometric constructions (e.g., two lines, two planes, a line and a plane, two curved surfaces, a line and a curved surface or the like) in which the two geometric constructions are substantially non-intersecting as they extend substantially to infinity. For example, as used herein, a planar surface (i.e., a two-dimensional surface) is said to be parallel to a line when every point along the line is spaced apart from the nearest portion of the surface by a substantially equal distance. Similarly, a line is said to be parallel to a curved surface when the line and the curved surface do not intersect as they extend to infinity and when every point along the line is spaced apart from the nearest portion of the curved surface by a substantially equal distance. Two geometric constructions are described herein as being "parallel" or "substantially parallel" to each other when they are nominally parallel to each other, such as for example, when they are parallel to each other within a tolerance. Such tolerances can include, for example, manufacturing tolerances, measurement tolerances or the like.

The terms "perpendicular," "orthogonal," and/or "normal" are used herein to describe a relationship between two geometric constructions (e.g., two lines, two planes, a line and a plane, two curved surfaces, a line and a curved surface or the like) in which the two geometric constructions intersect at an angle of approximately 90 degrees within at least one plane. For example, as used herein, a line is said to be normal to a curved surface when the line and a portion of the curved surface intersect at an angle of approximately 90 degrees within a plane. Two geometric constructions are described herein as being, for example, "perpendicular" or "substantially perpendicular" to each other when they are nominally perpendicular to each other, such as for example, when they are perpendicular to each other within a tolerance. Such tolerances can include, for example, manufacturing tolerances, measurement tolerances or the like.

As used herein, the term "flexible" is used to describe a structure having a first portion that is easily deflected, displaced and/or deformed with respect to a second portion of the structure when an external load is applied to the first portion of the structure. For example, a first surgical cable having a greater degree of flexibility is less resistant to deflection when exposed to a force than a second surgical cable having a lesser degree of flexibility. Thus, in some embodiments, the first (or more flexible) surgical cable can be more easily coiled and/or coiled to a smaller radius of curvature than the second (or less flexible) surgical cable.

The flexibility of an object is an extensive property of the object, and thus is dependent upon both the material from which the object is formed and/or certain physical characteristics of the object (e.g., the shape of portions of the object). For example, the flexibility of an object can be increased by constructing the object from a material having a low modulus of elasticity or a low flexural modulus. For example, a surgical cable constructed of urethane can be more flexible than a similar surgical cable constructed of stainless steel fibers, because the modulus of elasticity and/or the flexural modulus of urethane is significantly lower than the modulus of elasticity and/or the flexural modulus of stainless steel. The flexibility of an object can also be increased by changing a physical characteristic of the object and/or the components from which the object is constructed. In certain instances, the flexibility of an object can be increased by changing the shape and/or size of the components from which an object is constructed. For example, a surgical cable constructed of braided steel fibers can be more flexible than a similar surgical cable constructed from monolithically extruded steel, because the shape and/or size of the braided steel fibers can provide greater flexibility than a monolithic construction of the same material.

In certain instances, a flexible object can be an object that is easily elastically deformed when an external load is applied to the object. For example, in certain instances, a surgical cable constructed from an elastomeric material that can easily stretch (i.e., elastically deform), when an external load is applied to the object. In addition to being considered a flexible surgical cable, the surgical cable can also be considered as "elastic" or "resilient." In other instances, a flexible object can be an object that is easily plastically deformed when an external load is applied to the object. Such a flexible object can be characterized as "flexible" and "plastically deformable." One example of such a flexible and plastically deformable object is a thin metallic wire, such as, for example, a twist-tie. In yet other instances, a flexible object can be constructed from one or more components and/or materials characterized as "rigid." Said another way, in certain instances, a flexible object can be constructed from one or more components and/or materials having a high modulus of elasticity, a high flexural modulus, and/or a high yield strength. For example, in certain instances, a surgical cable can be constructed from multiple steel links that are coupled together such that the overall surgical cable is easily deflected, displaced and/or deformed when an external load is applied to the surgical cable. Although the individual links of such a surgical cable are not flexible, the overall cable can be described as flexible.

As used herein the term "sacral vertebra" refers to a vertebra associated with a sacrum of a spinal column. For example, the sacrum includes five vertebra fused together, referred to as the S1, S2, S3, S4, and S5 sacral vertebrae. The S1 sacral vertebra is superior to the S2 sacral vertebra, the S2 sacral vertebra is superior to the S3 sacral vertebra and so on. As used herein the term "lumbar vertebra" refers to the L1-L5 vertebrae of the spinal column, with the L5 lumbar vertebra being superior to the S1 sacral vertebra, the L4 lumbar vertebra being superior to the L5 vertebra, the L3 vertebra being superior to the L4 vertebra and so on. As used herein, the terms "vertebra" and "vertebrae" used without a modifier can refer to any type of vertebra or vertebrae (e.g., sacral, lumbar, thoracic, cervical).

Figure 1:
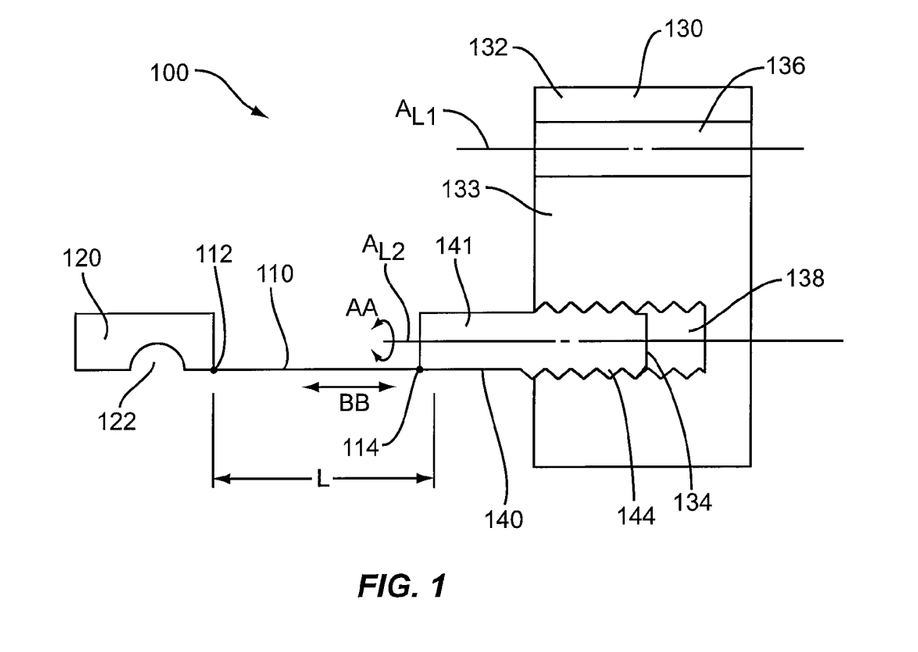
FIG. 1 is a schematic illustration of a medical device according to an embodiment.

FIG. 1 is a schematic illustration of a cross-section of a medical device 100 according to an embodiment. The medical device 100 includes a surgical cable 110, a coupling member 120 and an adjustment mechanism 130. The coupling member 120 defines an opening 122 and is coupled to a first end portion 112 of the surgical cable 110. The coupling member 120 can be coupled to the first end portion 112 of the surgical cable 110 by any suitable mechanism. For example, in some embodiments, the coupling member 120 can be coupled to the first end portion 112 of the surgical cable 110 by a crimp joint, an adhesive, a weld, a solder joint, and/or the like. In other embodiments, the coupling member 120 can be coupled to the first end portion 112 of the surgical cable 110 by tying the first end portion 112 of the surgical cable 110 to the coupling member 120.

As described in more detail herein, the opening 122 is configured to receive a portion of a fastener (not shown in FIG. 1). For example, in some embodiments, the opening 122 is configured to receive a portion of a bone fixation device (e.g., a bone screw). Moreover, when such a fastener is received within the opening 122, movement of the coupling member 120 relative to the fastener is limited. In this manner, the coupling member 120 can be used to couple the first end portion 112 of the surgical cable 110 to an object, such as, for example, a bone tissue.

The adjustment mechanism 130 includes a housing 132 and an elongate member 140. The housing 132 has a side wall 133 that defines a first opening 136 having a longitudinal axis $AL_1$ and a second opening 138 having a longitudinal axis $AL_2$. The side wall 133 includes a threaded portion 134 within the second opening 138. Said another way, the side wall 133 defines female threads 134 within the second opening 138. Although the longitudinal axis $AL_1$ is shown as being substantially parallel to the longitudinal axis $AL_2$, in other embodiments, the longitudinal axis $AL_1$ can be non-parallel to the longitudinal axis $AL_2$. In yet other embodiments, the longitudinal axis $AL_1$ can be substantially perpendicular to the longitudinal axis $AL_2$.

The first opening 136 is configured to receive a portion of a fastener (not shown in FIG. 1). For example, in some embodiments, the first opening 136 is configured to receive a portion of a bone fixation device (e.g., a bone screw). Moreover, when such a fastener is received within the first opening 136, movement of the housing 132 relative to the fastener is limited. In this manner, the housing 132 can be used to couple the second end portion 114 of the surgical cable 110 to an object, such as, for example, a bone tissue.

The elongate member 140 includes an end portion 141 and a threaded portion 144. The threaded portion 144 of the elongate member 140 corresponds to (i.e., has substantially the same nominal size and thread pitch) the threaded portion 134 of the second opening 138 of the housing 132. Similarly stated, the threaded portion 144 of the elongate member 140 includes male threads that correspond to the female threads of the threaded portion 134 of the housing 132. In this manner, the elongate member 140 can be threadedly coupled to the housing 132. More particularly, the threaded portion 144 of the elongate member 140 can be threadedly disposed within the second opening 138 of the housing 132.

The end portion 141 of the elongate member 140 is coupled to the second end portion 114 of the surgical cable 110. In this manner, the second end portion 114 of the surgical cable 110 is coupled to the housing 132 via the elongate member 140. The elongate member 140 can be coupled to the second end portion 114 of the surgical cable 110 by any suitable mechanism. For example, in some embodiments, the elongate member 140 can be coupled to the second end portion 114 of the surgical cable 110 by a crimp joint, an adhesive, a weld, a solder joint, and/or the like. In other embodiments, the elongate member 140 can be coupled to the second end portion 114 of the surgical cable 110 by tying the second end portion 114 of the surgical cable 110 to the end portion 141 of the elongate member 140.

As described in more detail herein, the medical device 100 can be used to secure tissue within the body. More particularly, in some embodiments, the medical device can be used to stabilize a portion of a spinal column. For example, in some embodiments, the elongate member 140 can be rotated within the housing 132 as shown by the arrow AA. When the elongate member 140 rotates relative to the housing 132, the elongate member 140 is moved along the longitudinal axis $AL_2$ within the second opening 138, as shown by the arrow BB. In this manner, a length L and/or a tension of the surgical cable 110 can be adjusted. Similarly stated, this arrangement allows the length L and/or the tension of the surgical cable 110 to be changed in a controlled and/or incremental manner.

As described in more detail herein, in some embodiments, the coupling member 120 is used to couple the first end portion 112 of the surgical cable 110 to a first portion of a spinal column (not show in FIG. 1), such as for example, a pedicle, a portion of an ilium, or the like. Similarly, the housing 132 is used to couple the second end portion 114 of the surgical cable 110 to a second portion of a spinal column, such as for example, a pedicle, a portion of an ilium, or the like. A portion of the surgical cable 110 can be disposed adjacent a third portion of a spinal column, such as, for example a spinous process. Similarly stated, when the first end portion 112 of the surgical cable 110 is coupled to the first portion of the spinal column and the second end portion 114 of the surgical cable 110 is coupled to the second portion of the spinal column, a portion of the surgical cable 110 can be in contact with, wrapped about and/or disposed against the third portion of the spinal column. Thus, when the length L and/or the tension of the surgical cable 110 is changed, the portion of the surgical cable 110 can exert a force against the third portion of the spinal column.

The surgical cable 110 can be any flexible member suitable for securing tissue within the body. Thus, the surgical cable 110 can include any cable, tether, strap, sling, suture, and/or similar flexible structure for securing tissue within the body. In some embodiments, for example, the surgical cable 110 can be any flexible member suitable for being coupled to portions of a spine to stabilize the spinal column. For example, in some embodiments, the surgical cable 110 can be constructed from a flexible and substantially inelastic material, such as steel wire. In other embodiments, the surgical cable 110 can be constructed from a flexible and substantially elastic material, such as an elastic polymer. In some embodiments, the surgical cable 110 can be constructed from multiple components that are individually formed. For example, in some steel fibers that are wound and/or braided together. In other embodiments, the surgical cable 110 can include an inner core (e.g., constructed from stainless steel) and an outer layer (e.g., constructed from a polymer such as, for example, polyester, nylon, polypropylene, polyethylene and/or the like). In yet other embodiments, the surgical cable 110 can be a monolithically constructed from a single material.

Figure 2:
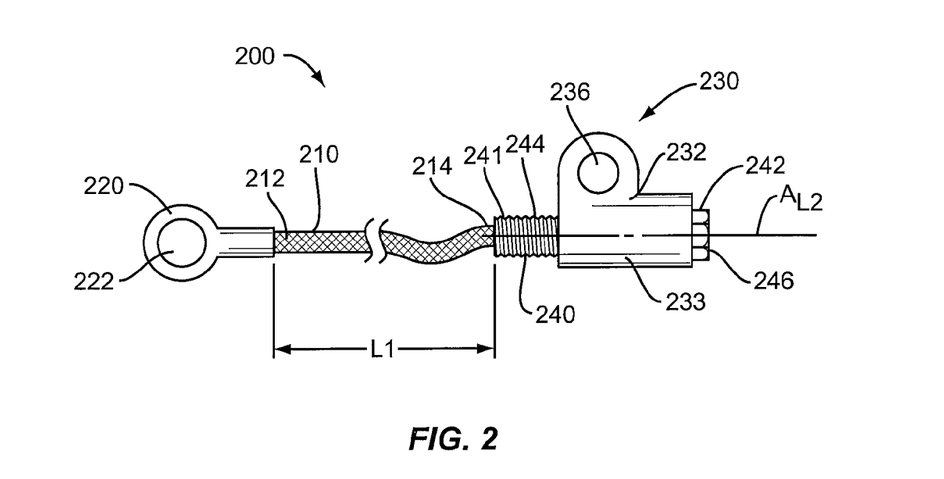
FIGS. 2 and 3 are top plan views of a medical device according to an embodiment in a first configuration and second configuration, respectively.
Figure 3:
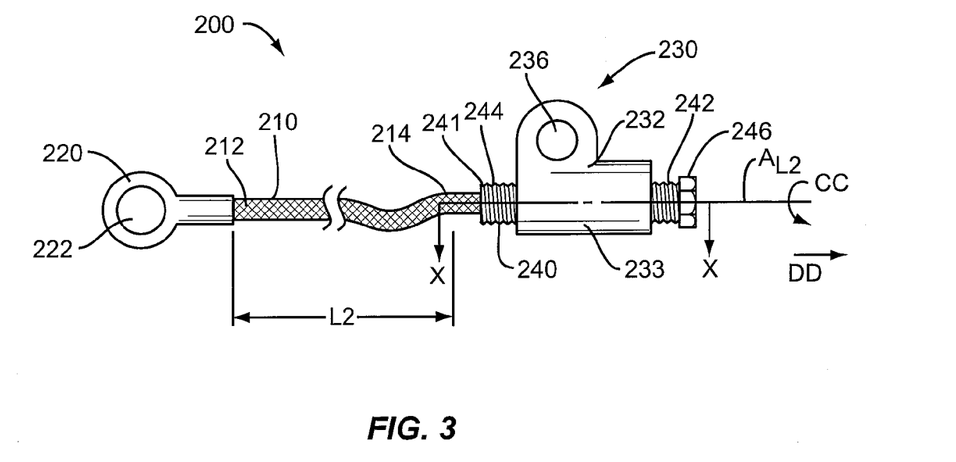
Figure 4:
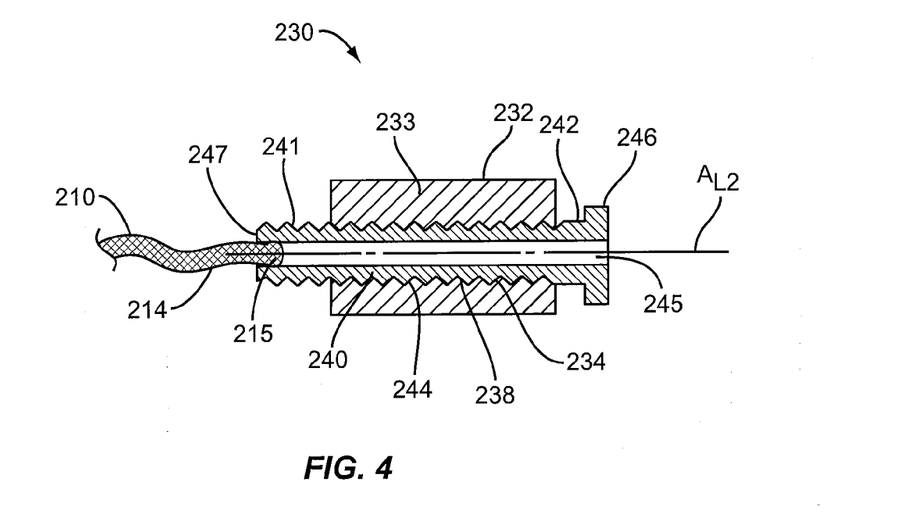
FIG. 4 is a cross-sectional view of a portion of the medical device shown in FIGS. 2 and 3 taken along line X-X in FIG. 3.

FIGS. 2 and 3 are top plan views of a medical device 200 according to an embodiment in a first configuration and second configuration, respectively. FIG. 4 is a cross-sectional view of a portion of the medical device 200 taken along line X-X in FIG. 3. The medical device 200 includes a surgical cable 210, a coupling member 220 and an adjustment mechanism 230. The surgical cable 210 is a flexible member suitable for securing and/or stabilizing tissue within a body, as described above. The surgical cable 210 has a first end portion 212, a second end portion 214 and a central portion (not identified in FIGS. 2-4) disposed therebetween. As shown in FIG. 4, the second end portion 214 of the surgical cable 210 includes an enlarged portion 215. The enlarged portion 215 has a size (e.g., a diameter) greater than a size of the remainder of the surgical cable 210.

The coupling member 220 defines an opening 222 and is coupled to the first end portion 212 of the surgical cable 210. In some embodiments, for example, the coupling member 220 can be an eyelet. The coupling member 220 can be coupled to the first end portion 212 of the surgical cable 210 by any suitable mechanism, as described above. The opening 222 is configured to receive a portion of a fastener (not shown in FIGS. 2 and 3), such as, for example a bone screw. In this manner, the coupling member 220 can be used to couple the first end portion 212 of the surgical cable 210 to an object, such as, for example, a bone tissue.

The adjustment mechanism 230 includes a housing 232 and an elongate member 240. The housing 232 has a side wall 233 that defines a first opening 236 having a longitudinal axis (not shown in FIGS. 2 and 3) and a second opening 238 (see e.g., FIG. 4) having a longitudinal axis $AL_2$. The longitudinal axis is substantially perpendicular to the longitudinal axis $AL_2$. The first opening 236 is configured to receive a portion of a fastener (not shown in FIGS. 2-4), such as, for example, a bone screw. In this manner, the housing 232 can be coupled to an object, such as, for example, a bone tissue. The side wall 233 includes a threaded portion 234 within the second opening 238. Said another way, the side wall 233 defines female threads 234 within the second opening 238.

The elongate member 240 includes a first end portion 241, a second end portion 242, and a threaded portion 244. The threaded portion 244 of the elongate member 240 corresponds to (i.e., has substantially the same nominal size and thread pitch) the threaded portion 234 of the second opening 238 of the housing 232. In this manner, the threaded portion 244 of the elongate member 240 can be threadedly disposed within the second opening 238 of the housing 232. Moreover, when the elongate member 240 is coupled to the housing 232, the first end portion 241 is disposed outside of the housing 232 on a first side of the housing 232 and the second end portion 242 is disposed outside of the housing 232 on a second side of the housing 232 opposite the first side.

The first end portion 241 of the elongate member 240 is coupled to the second end portion 214 of the surgical cable 210. More particularly, as shown in FIG. 4, the elongate member 240 defines a lumen 245 within which the enlarged portion 215 of the surgical cable 210 is disposed. The first end portion 241 of the elongate member 240 includes a shoulder 247 having a size (e.g., an inner diameter) that is smaller than a size (e.g., an inner diameter) of the lumen 245 and/or the enlarged portion 215 of the surgical cable 210. In this manner, the when the enlarged portion 215 of the surgical cable 210 is disposed within the lumen 245, the shoulder 247 contacts the enlarged portion 215 to limit the axial movement of the surgical cable 210 relative to the elongate member 240. Thus, the second end portion 214 of the surgical cable 210 is coupled to the housing 232 via the elongate member 240.

Although the engagement of the shoulder 247 and the enlarged portion 215 of the surgical cable 210 limits axial movement of the of the surgical cable 210 relative to the elongate member 240, in some embodiments this arrangement can allow the elongate member 240 to rotate relative to the surgical cable 210. For example, in some embodiments, the elongate member 240 can include a bearing (not shown in FIGS. 2-4) to facilitate rotation of the elongate member 240 relative to the surgical cable 210. In this manner, when the elongate member 240 is rotated about the longitudinal axis $AL_2$ within the housing 232, the rotation of the surgical cable 210 is limited. This arrangement can prevent the surgical cable 210 from being twisted during use.

The second end portion 242 of the elongate member 240 includes a tool engagement portion 246. The tool engagement portion 246 includes a hexagonal shaped outer surface configured to be received within an insertion tool and/or an adjustment tool. In this manner, as described below, the insertion tool and/or the adjustment tool can be used to move the elongate member 240 within the housing 232. Although the tool engagement portion 246 is shown as including a hexagonal shaped outer surface, in other embodiments, the tool engagement portion 246 can include a keyed recess configured to receive a corresponding protrusion from an insertion tool. In yet other embodiments, the tool engagement portion 246 can include a snap ring, clip, E-ring or any other suitable mechanism for removably coupling the elongate member 240 to an insertion tool and/or an adjustment tool.

The medical device 200 can be moved between a first configuration (FIG. 2) and a second configuration (FIG. 3). When the medical device 200 is in the first configuration, the elongate member 240 is in a first position within the housing 232. Moreover, when the medical device 200 is in the first configuration, the surgical cable 210 has a first length L1. Similarly stated, when the medical device 200 is in the first configuration, the opening 222 of the coupling member 220 is spaced apart from the opening 236 of the adjustment mechanism 230 by a first distance.

The medical device 200 can be moved from the first configuration to the second configuration by rotating the elongate member 240 within the housing 232 as shown by the arrow CC in FIG. 3. When the elongate member 240 rotates relative to the housing 232, the elongate member 240 is moved along the longitudinal axis $AL_2$ within the second opening 238, as shown by the arrow DD. When the medical device 200 is in the second configuration, the elongate member 240 is in a second position within the housing 232. Moreover, when the medical device 200 is in the second configuration, the surgical cable 210 has a second length L2 different from the first length L1. In some embodiments, the second length L2 can be less than the first length L1. Similarly stated, when the medical device 200 is in the second configuration, the opening 222 of the coupling member 220 is spaced apart from the opening 236 of the adjustment mechanism 230 by a second distance. This arrangement allows the length and/or the tension of the surgical cable 210 to be adjusted. Similarly stated, this arrangement allows the length L and/or the tension of the surgical cable 210 to be changed within the body in situ.

Figure 5:
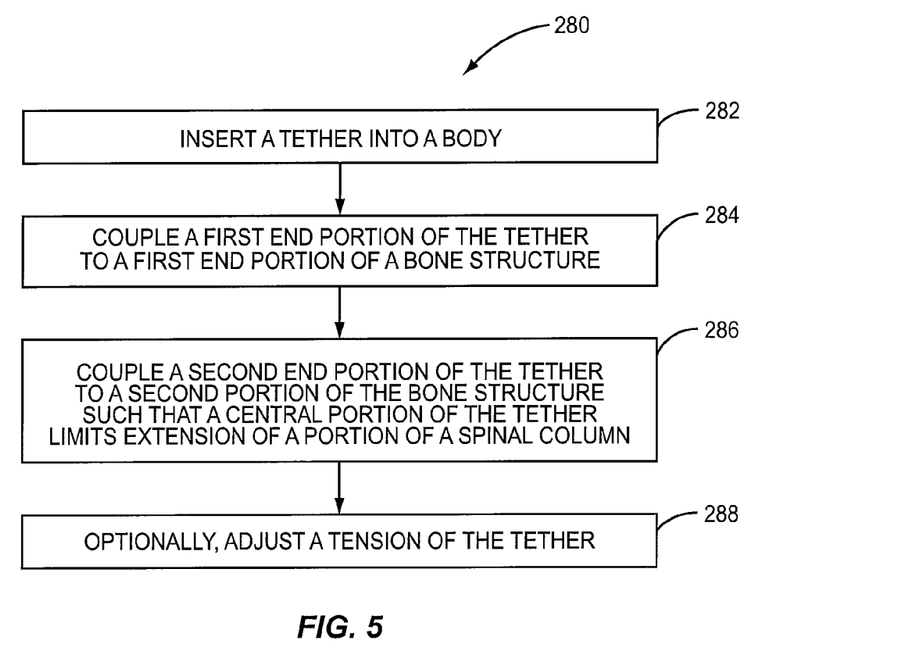
FIG. 5 is a flow chart of a method of inserting the medical device shown in FIGS. 2 and 3 into the body according to an embodiment.

FIG. 5 is a flow chart of a method 280 for securing and/or stabilizing a bodily tissue, according to an embodiment. The method illustrated in FIG. 5 is discussed with reference to FIGS. 6-8, which are posterior views of the medical device 200 (as discussed with reference to FIGS. 2-4) disposed within a body B in various positions and/or configurations. Although the method of FIG. 5 is described as being performed using the medical device 200, in other embodiments, the method of FIG. 5 can be performed using other suitable medical devices, such as any of the medical devices shown and described herein.

Figure 6:
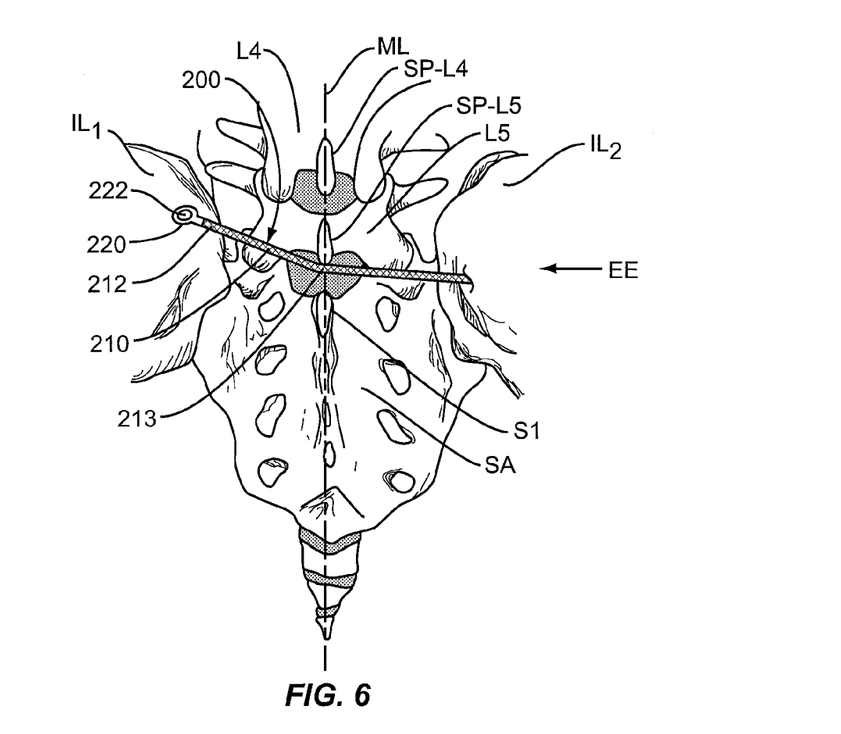
FIGS. 6-8 are posterior views of a portion of a spinal column having the medical device shown in FIGS. 2 and 3 coupled thereto according to the method illustrated in FIG. 5.

The illustrated method includes inserting a tether into a body, at 282. Referring to FIG. 6, the tether can be at least a portion of the surgical cable 210 of the medical device 200, and can be inserted such that the first end portion 212 of the surgical cable 210 is the first portion of the surgical cable 210 to enter the body B. The surgical cable 210 can be inserted in any suitable manner. For example, in some embodiments, the surgical cable 210 can be inserted into the body percutaneously and/or in a minimally-invasive manner. In some embodiments, the surgical cable 210 can be inserted through a lateral skin incision (i.e., a skin incision offset from the mid-line axis ML of the spinal column), and moved laterally within the body, as shown by the arrow EE in FIG. 6. In some embodiments, the lateral skin incision can have a length of between 3 mm and 25 mm. In some embodiments, for example, the lateral skin incision can have a length of approximately 15 mm. Moreover, in some embodiments, the surgical cable 210 can be inserted into the body via a cannula (not shown in FIGS. 6-8). In some embodiments, such a cannula can have a size of between 3 mm and 25 mm. In some embodiments, for example, the size of the cannula can be approximately 15 mm.

In some embodiments, the surgical cable 210 can be inserted into the body using an insertion tool (not shown in FIGS. 6-8) configured to pierce, dilate and/or displace bodily tissue. For example, in some embodiments, the coupling member 220 of the medical device 200 can be removably coupled to an insertion tool configured to define a passageway (not identified in FIGS. 6-8) within the body B through which the surgical cable 210 can be disposed. In some embodiments, the passageway can include an opening defined in the interspinous ligament and/or other bodily tissue surrounding the vertebrae (not shown). In this manner, a central portion 213 of the surgical cable 210 can be disposed adjacent an inferior side of the spinous processes SP of the L5 vertebra. Thus, as described in more detail herein, the central portion 213 of the surgical cable 210 can contact the inferior side of the spinous processes SP-L5 via the interspinous ligament. For purposes of clarity, however, the tissue surrounding the spinous processes SP-L5, SP-L4 is not illustrated. In other embodiments, the method can optionally include inserting a guide member (e.g., a guide wire, a Kirschner wire or the like) to define a passageway within the body B before the surgical cable 210 is disposed within the body B.

Figure 7:
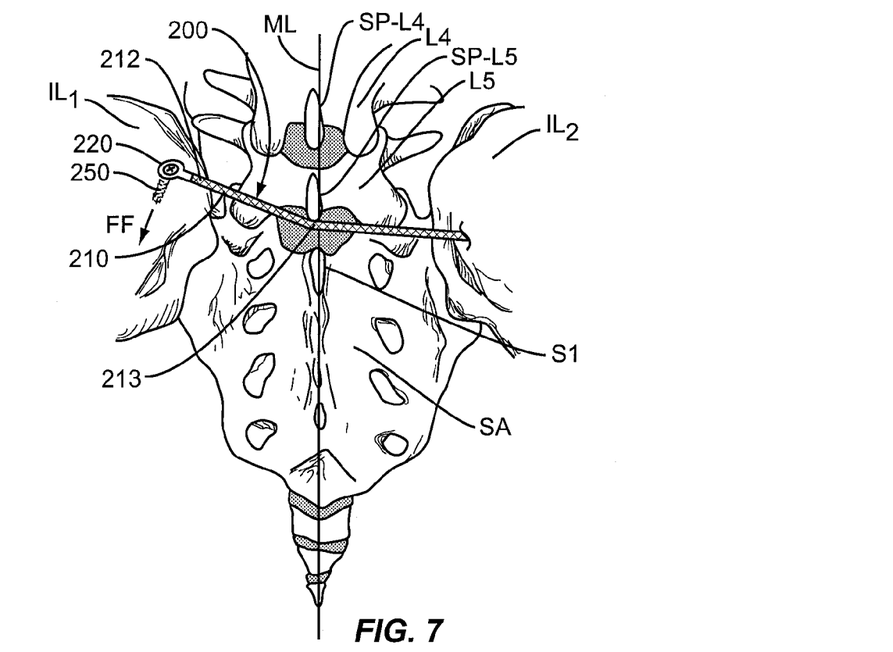

Returning to the flow chart shown in FIG. 5, a first end portion of the tether is coupled to a first portion of a bone structure, at 284. Referring to FIG. 7, the first portion of the bone structure, can be, for example, a portion of the ilium $IL_1$ disposed on a first side of the mid-line axis ML. The first end portion 212 of the surgical cable 210 can be coupled to the first portion of the ilium $IL_1$ via the coupling member 220. More particularly, the first end portion 212 of the surgical cable 210 can be coupled to the first portion of the ilium $IL_1$ by disposing a bone screw 250 through the opening 222 of the coupling member 220. A distal end of the bone screw 250 is then advanced into the first portion of the ilium $IL_1$, as shown by the arrow FF in FIG. 7, to secure the first end portion 212 of the surgical cable 210 to the first portion of the ilium $IL_1$. In some embodiments, for example, the first end portion 212 of the surgical cable 210 can be coupled to the first portion of the ilium $IL_1$ via a mid-line incision (i.e., a skin incision substantially aligned with the mid-line axis ML of the spinal column). For example, in some embodiments, the bone screw 250 can be inserted into the body and advanced into the first portion of the ilium $IL_1$ through a mid-line incision using an insertion tool.

Figure 8:
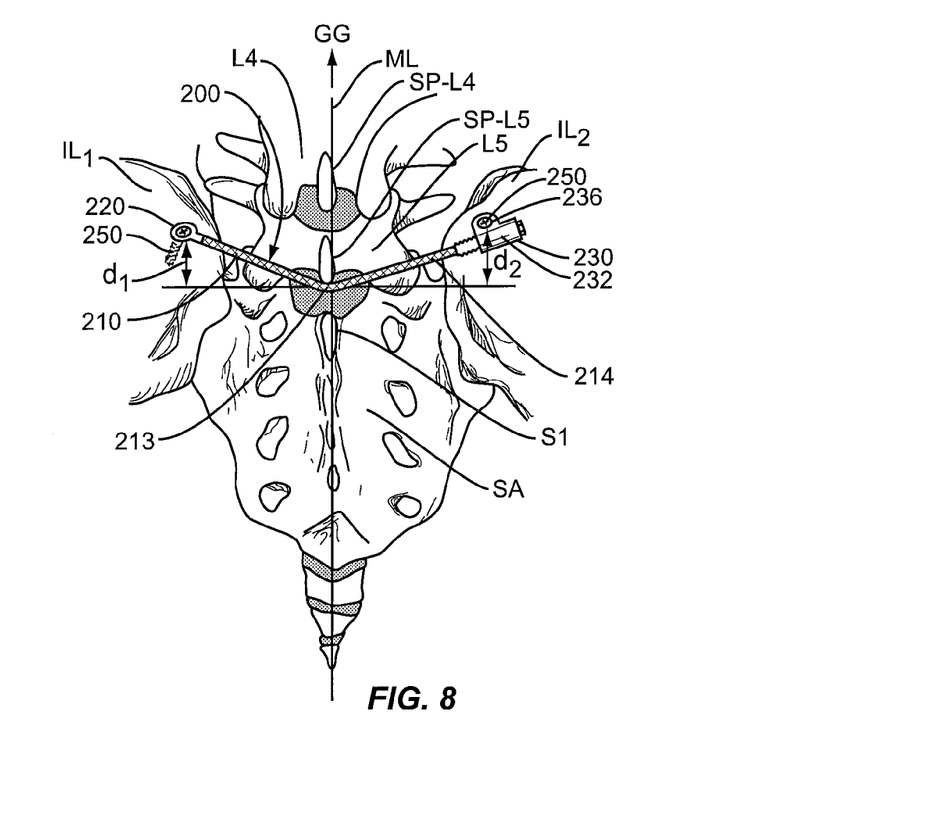

Returning to the flow chart shown in FIG. 5, a second end portion of the tether is coupled to a second portion of the bone structure such that a central portion of the tether limits extension of a portion of a spinal column associated with the bone structure, at 286. Referring to FIG. 8, the second portion of the bone structure, can be, for example, a second portion of the ilium $IL_2$ disposed on a second side of the mid-line axis ML. The second end portion 214 of the surgical cable 210 can be coupled to the second portion of the ilium $IL_2$ via the adjustment mechanism 230. More particularly, the second end portion 214 of the surgical cable 210 can be coupled to the second portion of the ilium $IL_2$ by disposing a bone screw 250 through the opening 236 of the housing 232. A distal end of the bone screw 250 is then advanced into the second portion of the ilium $IL_2$ to secure the second end portion 214 of the surgical cable 210 to the second portion of the ilium $IL_2$. In some embodiments, for example, the second end portion 214 of the surgical cable 210 can be coupled to the second portion of the ilium $IL_2$ via a mid-line incision (i.e., a skin incision substantially aligned with the mid-line axis ML of the spinal column). For example, in some embodiments, the bone screw 250 can be inserted into the body and advanced into the second portion of the ilium $IL_2$ through a mid-line incision using an insertion tool. In some embodiments, the mid-line incision through which the second end portion 214 of the surgical cable 210 is coupled to the second portion of the ilium $IL_2$ is the same as the mid-line incision through which the first end portion 212 of the surgical cable 210 is coupled to the first portion of the ilium $IL_1$.

As shown in FIG. 8, in some embodiments, the first end portion 212 of the surgical cable 210 can be coupled to the first portion of the ilium $IL_1$ and the second end portion 214 of the surgical cable 210 can be coupled to the second portion of the ilium $IL_2$ such that the central portion 213 of the surgical cable 210 is disposed adjacent an inferior side of the spinous process SP-L5. In this manner, the surgical cable 210 can limit extension of a portion of the spinal column. More particularly, this arrangement can limit the extension of the L5 spinous process relative to the S1 vertebra of the sacrum SA. Moreover, this arrangement allows flexion of the portion of the spinal column.

By limiting the extension of spinal column while allowing flexion of the spinal column in the L5-S1 region, the surgical cable 210 dynamically stabilizes a portion of the spinal column. Similarly stated, the surgical cable 210 stabilizes a portion of the spinal column while allowing relative movement between the L5 and S1 vertebrae. Moreover, the extension between the L5 and S1 vertebrae can be adjusted as a function of the length of the surgical cable 210, the tension of the surgical cable 210, the offset d1 (see FIG. 8) between the location of the first end portion 212 of the surgical cable 210 and the inferior side of the spinous processes SP-L5 in a direction parallel to the mid-line axis ML, the offset d2 (see FIG. 8) between the location of the second end portion 214 of the surgical cable 210 and the inferior side of the spinous processes SP-L5 in a direction parallel to the mid-line axis ML, an elasticity of the surgical cable 210, a strength of the surgical cable 210, and/or the like. For example, in some embodiments, the surgical cable 210 can have a high elasticity such that the L5 spinous process SP-L5 can initially move towards the S1 vertebra during extension. As the surgical cable 210 elastically deforms, however, the amount of movement of the L5 vertebra is limited. In this manner, the surgical cable 210 can limit movement of a portion of the spinal column without acting as a "hard stop." Similarly stated, the arrangement of the surgical cable 210 as described herein dynamically stabilizes the portion of the spinal column.

Returning to the flow chart shown in FIG. 5, in some embodiments, the illustrated method optionally includes adjusting a tension of the tether, at 288. Referring again to FIG. 8, the tension of the surgical cable 210 can be adjusted via the adjustment mechanism 230, as discussed above. The tension of the surgical cable 210 can be adjusted, for example, by adjusting the length of the surgical cable 210. More particularly, the tension of the surgical cable 210 can be adjusted by adjusting the length of the surgical cable 210 between the coupling member 220 and the adjustment mechanism 230. By adjusting the length and/or the tension of the surgical cable 210, the amount of movement between the L5 and S1 vertebrae during extension of the spinal column that is allowed by the medical device 200 can be adjusted. Moreover, in some embodiments, adjusting the length and/or the tension of the surgical cable 210 can result in the central portion 213 of the surgical cable applying a force on the spinous process SP-L5 of the L5 vertebra, as shown by the arrow GG in FIG. 8. In some embodiments, for example the spinous process SP-L5 can be moved in a cephalic direction when the length and/or the tension of the surgical cable 210 is increased. Similarly stated, in some embodiments, the medical device 200 can be used to distract a spinous process.

In some embodiments, the method can optionally include maintaining the tension and/or the length of the surgical cable 210 after the tension and/or the length of the surgical cable 210 has been adjusted. In some embodiments, for example, the adjustment mechanism 230 can include a locking member configured to maintain the tension and/or the length of the surgical cable 210. Such a locking member can include, for example, a lock nut disposed about the elongate member 240, a lock washer disposed about the elongate member 240, a ratchet and pawl combination to limit rotation of the elongate member 240 relative to the housing 232 in at least one direction, and/or the like. In some embodiments, the threaded portion 244 of the elongate member 240 can have a different nominal size and/or thread pitch than the threaded portion 234 of the housing 232. In this manner, after the elongate member 240 is rotated within the housing 232, the interference between the threaded portion 244 of the elongate member 240 and the threaded portion 234 of the housing 232 can limit further the movement of the elongate member 240 within the housing 232.

Although the tension of the surgical cable 210 is generally described above as being increased (e.g., to exert a force upon the spinous process SP-L5), in some embodiments, the tension of the surgical cable 210 can be decreased. Similarly stated, in some embodiments, the method can include increasing the length of the surgical cable 210. In this manner, for example, medical device 200 can be adjusted to allow a greater amount of movement between the L5 and S1 vertebrae during extension of the spinal column.

Figure 9:
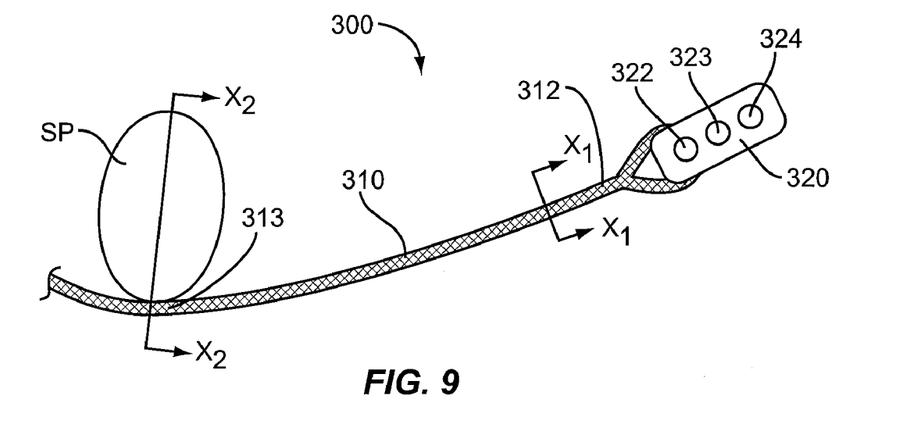
FIG. 9 is a top plan view of a portion of a medical device according to an embodiment.
Figure 10:
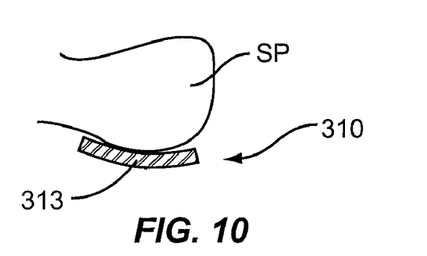
FIGS. 10 and 11 are cross-sectional views of a portion of the medical device shown in FIG. 9 taken along lines $X_1$-$X_1$ and $X_2$-$X_2$, respectively.
Figure 11:
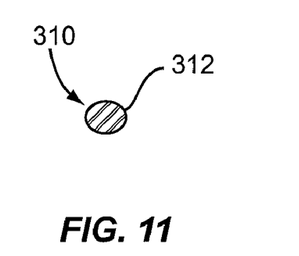

FIG. 9 is a top plan view of a portion of a medical device 300 according to an embodiment. FIGS. 10 and 11 are cross-sectional views of the medical device 300 taken along lines $X_1$-$X_1$ and $X_2$-$X_2$ in FIG. 9, respectively. The medical device 300 includes a coupling member 320 and a surgical cable 310. The surgical cable 310 can be any cable, tether, strap, sling, suture, or similar flexible structure for securing tissue within the body, as described herein. The surgical cable 310 has a first end portion 312 and a central portion 313. As described above and as shown in FIG. 9, the surgical cable 310 can be disposed within the body such that the central portion 313 of the surgical cable 310 is adjacent to and/or in contact with a spinous process SP. The surgical cable 310 has a cross-sectional area that varies along the length of the surgical cable 310. More particularly, as shown in FIG. 10, the cross-sectional area of the first end portion 312 of the surgical cable 310 is substantially circular. In contrast, as shown in FIG. 11, the cross-sectional area of the central portion 313 of the surgical cable 310 is substantially non-circular. More particularly, the cross-sectional area of the central portion 313 of the surgical cable 310 is substantially rectangular. In this manner, the central portion 313 of the surgical cable 310 provides a greater surface area for contacting the spinous process SP than does the first end portion 312 of the surgical cable 310.

Similarly stated, the central portion 313 of the surgical cable 310 provides a sling-like surface for contacting the spinous process SP and/or exerting a force upon the spinous process SP.

The coupling member 320 is coupled to the first end portion 312 of the surgical cable 310, by any suitable mechanism, as described above. The coupling member 320 defines a first opening 322, a second opening 323 and a third opening 324. Each of the first opening 322, the second opening 323 and the third opening 324 are configured to receive a portion of a fastener (not shown in FIG. 9), such as, for example a bone screw. In this manner, the coupling member 320 can be used to couple the first end portion 312 of the surgical cable 310 to an object, such as, for example, a bone tissue.

As shown in FIG. 9, the first opening 322, the second opening 323 and the third opening 324 are spaced longitudinally apart from each other. This arrangement allows the coupling member 320 to be coupled to an object (e.g., a bone tissue) in any one of three distinct locations, as determined by the locations of the openings. Similarly stated, this arrangement provides the coupling member 320 with a "coarse adjustment" feature. For example, in some embodiments, a bone screw can be inserted into a bone tissue at a predetermined location. The coupling member 320 can then be placed such that the head of the bone screw is within any one of the first opening 322, the second opening 323 and/or the third opening 324, as is desired to achieve a desired length of the surgical cable 310.

Figure 12:
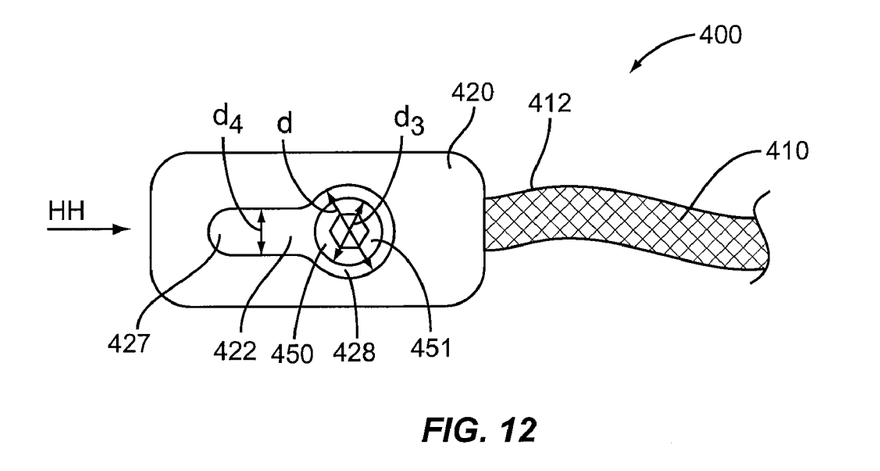
FIG. 12 is a top plan view of a portion of a medical device according to an embodiment.

Although the method 280 shown and described above includes disposing a bone screw 250 within the opening 222 of the coupling member 220 before inserting the bone screw 250 into the bone tissue, in other embodiments, a method can include first inserting a bone screw into the bone tissue, followed by disposing the head of the bone screw 250 within an opening of a coupling member. FIG. 12 is a top view of a portion of a medical device 400 that can be used in such a method. The medical device 400 includes a coupling member 420, a surgical cable 410 and a bone screw 450. The surgical cable 410 can be any cable, tether, strap, sling, suture, or similar flexible structure for securing tissue within the body, as described herein. As described above, the surgical cable 410 can be disposed within the body such that a portion of the surgical cable 410 can stabilize and/or secure a tissue within the body.

The coupling member 420 is coupled to a first end portion 412 of the surgical cable 410 by any suitable mechanism, as described above. The coupling member 420 defines an opening 422 having a substantially circular portion 428 and a slotted portion 427. The substantially circular portion 428 has a diameter d that is larger than a diameter d3 of a head 451 of the bone screw 450. In this manner, the substantially circular portion 428 of the opening 422 can be disposed about the head 451 of the bone screw 450 after the bone screw 450 is inserted into a bone tissue. The slotted portion 427 of the opening has a lateral size d4 that is smaller than the diameter d3 of the head 451 of the bone screw 450 and is larger than a diameter of a shank (not shown in FIG. 12) of the bone screw 450. In this manner, after the substantially circular portion 428 of the opening 422 is disposed about the head 451 of the bone screw 450, the coupling member 420 can be moved relative to the bone screw 450, as shown by the arrow HH, to retain the coupling member 420 about the head 451 of the bone screw 450.

Figure 13:
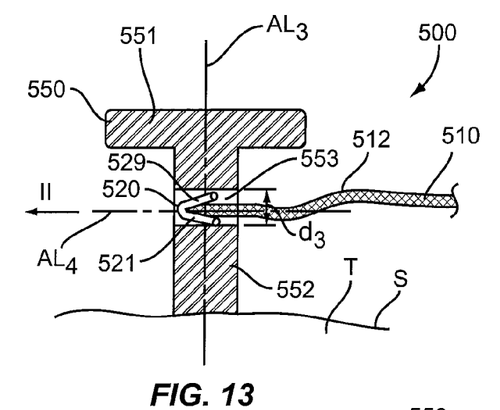
FIGS. 13 and 14 are side views of a portion of a medical device according to an embodiment, in a first configuration and a second configuration, respectively.
Figure 14:
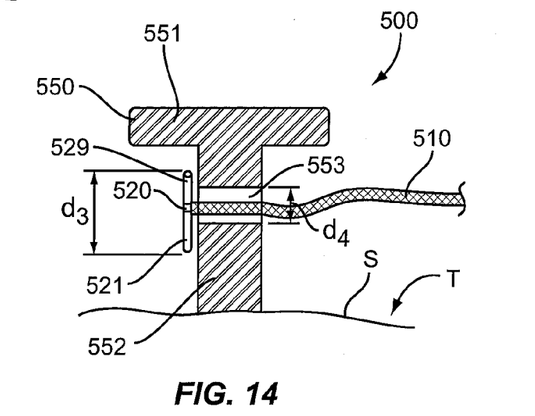

Although the coupling members are shown and described above as including one or more openings within which a portion of a bone screw can be disposed, in other embodiments, a coupling member need not define an opening. For example, FIGS. 13 and 14 are cross-sectional side views of a portion of a medical device 500 according to an embodiment, in a first configuration and a second configuration, respectively. The medical device 500 includes a coupling member 520, a surgical cable 510 and a bone screw 550. The surgical cable 510 can be any cable, tether, strap, sling, suture, or similar flexible structure for securing tissue within the body, as described herein. As described above, the surgical cable 510 can be disposed within the body such that a portion of the surgical cable 510 can stabilize and/or secure a tissue within the body.

The bone screw 550 includes a head 551 and a shank 552. The shank 552 defines an opening 553 therethrough. A longitudinal axis $AL_4$ of the opening 553 is substantially normal to a longitudinal axis $AL_3$ of the shank 552. The bone screw 550 can be any suitable bone screw, such as, for example, a self-tapping bone screw. As described below, the bone screw 550 is used to couple the first end portion 512 of the surgical cable 510 to a bone tissue T.

The coupling member 520 is coupled to a first end portion 512 of the surgical cable 510 by any suitable mechanism, as described above. The coupling member 520 includes a substantially rigid first arm 521 and a substantially rigid second arm 529. The first arm 521 and the second arm 529 are movable with respect to the surgical cable 510 and each other between at least a first position (FIG. 13) and a second position (FIG. 14). When the first arm 521 and the second arm 529 are collectively in the first position, a maximum distance d3 between the first arm 521 and the second arm 529 is less than a diameter d4 of the opening 553 of the bone screw 550. In this manner, the coupling member 520 can be disposed within the opening 553 of the bone screw 550, as shown in FIG. 13. When the first arm 521 and the second arm 529 are collectively in the second position, a maximum distance d3' between the first arm 521 and the second arm 529 is greater than a diameter d4 of the opening 553 of the bone screw 550. In this manner, the coupling member 520 can engage a portion of the shank 552 of the bone screw 550, as shown in FIG. 14.

In use, the bone screw 550 is threaded into the bone tissue T such that the opening 553 of the shank 552 is disposed above the surface S of the bone tissue T. The bone screw 550 can be rotated such that the longitudinal axis $AL_4$ of the opening 553 is aligned with the passageway through which the first end portion 512 of the surgical cable 510 will be disposed. The coupling member 520 is then disposed through the opening 553 of the bone screw 550, as shown by the arrow II in FIG. 13, when the first arm 521 and the second arm 529 are collectively in the first position. The first arm 521 and the second arm 529 are then moved into the second position, as shown in FIG. 14. In some embodiments, the first arm 521 and the second arm 529 can be moved into the second position, for example, by allowing the first arm 521 and the second arm 529 to engage a portion of the shank 522 and then moving the surgical cable 510 in a direction opposite the direction shown by the arrow II. In other embodiments, the coupling member 520 can include a biasing member to bias the first arm 521 and the second arm 529 in the second position. When the first arm 521 and the second arm 529 are in the second position, the surgical cable 510 is coupled to the bone screw 550. More particularly, when the first arm 521 and the second arm 529 are in the second position, movement of the surgical cable 510 relative to the bone screw in at least one direction is limited.

Figure 15:
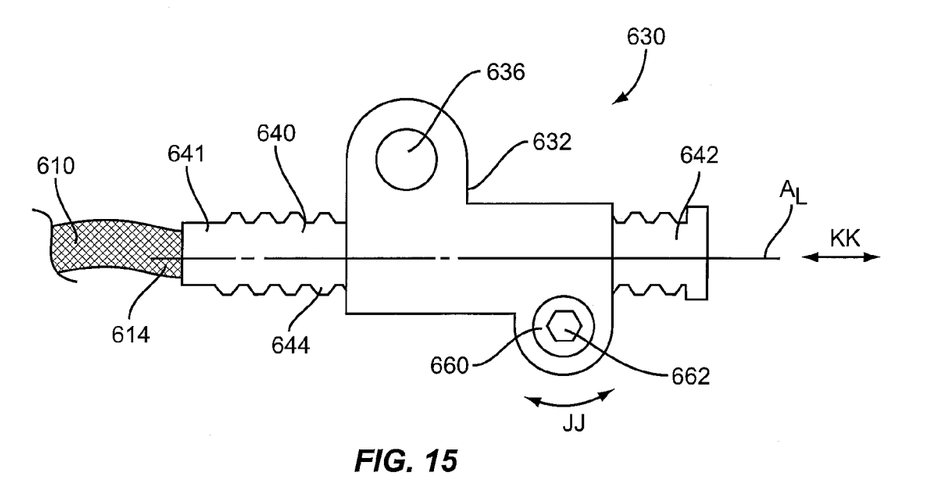
FIG. 15 is a top plan view of a portion of a medical device according to an embodiment.

Although the adjustment mechanism 230 is shown and described above as including an elongate member 240 having a tool engagement portion 246 that can be accessed via a lateral approach and/or along an axis substantially parallel to the longitudinal axis of the elongate member 240, in other embodiments, an adjustment mechanism can include a tool engagement portion that can be accessed via a posterior-anterior approach. Similarly stated, in other embodiments, an adjustment mechanism can include a tool engagement portion that can be accessed via an axis that is non-parallel to the longitudinal axis of the elongate member. For example, FIG. 15 is a top plan view of an adjustment mechanism 630 according to an embodiment. The adjustment mechanism 630 includes a housing 632, an elongate member 640 and a pinion 660. The housing 632 defines a first opening 636 and a second opening (not shown in FIG. 15). The first opening 636 is configured to receive a portion of a fastener (not shown in FIG. 15), such as, for example, a bone screw. In this manner, the housing 632 can be coupled to a bone tissue, as described above.

The elongate member 640 includes a first end portion 641, a second end portion 642, and a gear portion 644 (i.e., a rack portion). At least a portion of the elongate member 640 is movably disposed within the second opening of the housing 632. The first end portion 641 of the elongate member 640 is coupled to an end portion 614 of a tether 610. The tether 610 can be any cable, tether, strap, sling, suture, or similar flexible structure for securing tissue within the body, as described herein. In this manner, a tension and/or a length of the surgical cable 610 can be adjusted when the elongate member 640 moves within the housing 632 along a longitudinal axis AL of the elongate member 640.

The pinion 660 includes a tool engagement portion 662 and a gear portion (not shown in FIG. 15). The pinion 660 is coupled to the housing 632 such that a longitudinal axis (not shown in FIG. 15) of the pinion 660 is substantially normal to the longitudinal axis AL of the elongate member 640. Moreover, the longitudinal axis of the pinion 660 is substantially parallel to a longitudinal axis of the first opening 636. In this manner, the longitudinal axis of the pinion 660 can be substantially parallel to a posterior-anterior axis when the adjustment mechanism 630 is coupled to a portion of the spine.

The gear portion of the pinion 660 includes a plurality of gear teeth that correspond to (i.e., have substantially the same nominal size and pitch) the gear teeth included in the gear portion 644 of the elongate member 640. The pinion 660 is coupled to the housing 632 such that the gear portion (not shown in FIG. 15) of the pinion 660 is engaged with the gear portion 644 of the elongate member 640. In this manner, rotation of the pinion 660 about its longitudinal axis, as shown by the arrow JJ, results in translation of the elongate member 640, as shown by the arrow KK. Said another way, when the pinion 660 rotates about its longitudinal axis, the gear portion of the pinion 660 meshes with the gear portion 644 of the elongate member 640, thereby converting the rotational movement of the pinion 660 into translation movement of the elongate member 640 within the housing.

Although various embodiments have been described above, it should be understood that they have been presented by way of example only, and not limitation. Where methods described above indicate certain events occurring in certain order, the ordering of certain events may be modified. Additionally, certain of the events may be performed concurrently in a parallel process when possible, as well as performed sequentially as described above. Thus, the breadth and scope of the invention should not be limited by any of the above-described embodiments. While the invention has been particularly shown and described with reference to specific embodiments thereof, it will be understood that various changes in form and details may be made.

For example, although the first opening 136 is shown as being spaced apart from and/or distinct from the second opening 138, in other embodiments, an adjustment member can include a first opening that is contiguous (i.e., that shares a common boundary) with a second opening.

Although the elongate member 240 is shown as being rotatable within the housing 232 in both a clockwise and counter-clockwise direction, in other embodiments, an elongate member can be rotatable within a housing in only one direction. For example, in some embodiments, an elongate member can be rotatable only in a counter-clockwise direction, thus allowing the adjustment mechanism to increase the tension of a surgical cable, without allowing the adjustment mechanism to decrease the tension of the surgical cable. Similarly stated, in some embodiments, an elongate member can be translatable within a housing in only one direction. In such embodiments, the adjustment mechanism can include a ratchet and pawl combination to limit the rotation and/or translation of the elongate member in at least one direction.

Although various embodiments have been described as having particular features and/or combinations of components, other embodiments are possible having a combination of any features and/or components from any of embodiments as discussed above. For example, in some embodiments, a medical device can include a coupling member similar to the coupling member 320 (see e.g., FIG. 9), a surgical cable having a non-circular cross-sectional area, and an adjustment mechanism similar to the adjustment mechanism 630 (see e.g., FIG. 15). Furthermore, any of the various embodiments and applications of method 280 may employ any of the various embodiments of the medical devices disclosed herein.

What is claimed is:

1. An apparatus, comprising:
   a surgical cable having a first end portion and a second end portion;
   a coupling member coupled to the first end portion of the surgical cable, the coupling member defining an opening therethrough;
   an adjustment mechanism including a housing and a threaded elongate member, the housing defining a first opening and a second opening, a portion of a side wall of the housing defining a threaded portion within the second opening;
   the elongate member having a first end portion and an opposing second end portion, the first end portion of the elongate member coupled to the second end portion of the surgical cable;
   wherein the apparatus is configured to assume first and second states;
   wherein, in the first state, the first end portion of the elongate member is disposed outside the housing and the second end portion of the elongate member is disposed within the housing;
   wherein, in the second state, both the first and second end portions of the elongate member are disposed outside the housing;
   wherein in both first and second states, the elongate member is engaged with the threaded portion of the second opening.

2. The apparatus of claim 1, wherein:
   the first end portion of the elongate member is coupled to the second end portion of the surgical cable such that the elongate member can rotate relative to the surgical cable.

3. The apparatus of claim 1, wherein:
   the first end portion of the elongate member is coupled to the second end portion of the surgical cable such that rotation of the elongate member within the second opening of the housing causes the second end portion of the surgical cable to move in an axial direction relative to the housing.

4. The apparatus of claim 1, wherein:
   the elongate member is configured to rotate within the second opening of the housing in a first direction to adjust a length of the surgical cable between the coupling member and the housing;
   the elongate member is coupled to the housing such that rotation of the elongate member in a second direction is prevented.

5. The apparatus of claim 1, wherein the elongate member includes a tool engagement portion.

6. The apparatus of claim 1, wherein a longitudinal axis of the first opening of the housing is nonparallel to a longitudinal axis of the second opening of the housing.

7. The apparatus of claim 1, wherein a central longitudinal axis of the first opening of the housing is substantially parallel to and spaced apart from a central longitudinal axis of the second opening of the housing.

8. The apparatus of claim 1, wherein the surgical cable has a central portion having a non-circular cross-sectional shape.

9. The apparatus of claim 1, wherein the opening of the coupling member is a first opening from a plurality of openings defined by the coupling member.

10. The apparatus of claim 1, further comprising:
    a first bone screw having a distal end configured to be disposed through the opening of the coupling member and into a first bone structure; and
    a second bone screw having a distal end configured to be disposed through the first opening of the housing and into a second bone structure.

11. A method, comprising
    inserting a tether into a body;
    coupling a first end portion of the tether to a first bone structure;
    coupling a second end portion of the tether to a second bone structure such that a central portion of the tether is disposed adjacent an inferior side of a spinous process and applies a force in a cephalic direction to the inferior side of the spinous process, thereby limiting extension of a portion of a spinal column associated with the first and second bone structures while allowing flexion of the portion of the spinal column.

12. The method of claim 11, wherein the first bone structure is a first ilium disposed on a first side of a mid-line axis defined by the spinal column, and the second bone structure is a second ilium disposed on second side of the mid-line axis defined by the spinal column.

13. The method of claim 11, wherein the coupling the second end portion includes:
    adjusting a length of the tether between the first bone structure and the second bone structure.

14. The method of claim 11, wherein:
    the first end portion of the tether includes a coupling member defining an opening;
    the coupling the first end portion includes:
      disposing a bone screw through the opening defined by the coupling member; and
      advancing a portion of the bone screw into the first portion of the first bone structure.

15. A method comprising:
    inserting a tether percutaneously into a body via a lateral incision;
    coupling a first end portion of the tether to a first bone structure via a mid-line incision;

coupling a second end portion of the tether to a second bone structure such that a central portion of the tether limits extension of a portion of a spinal column associated with the first and second bone structures while allowing flexion of the portion of the spinal column.

16. A method, comprising:
inserting a tether into a body;
coupling a first end portion of the tether to a first ilium;
coupling a second end portion of the tether to a second ilium, such that a central portion of the tether is disposed adjacent an inferior side of an L5 spinous process;
adjusting a tension of the tether.

17. The method of claim 16, wherein:
the first end portion of the tether includes a coupling member defining an opening;
the coupling the first end portion includes:
disposing a bone screw through the opening defined by the coupling member;
advancing a portion of the bone screw into the first ilium.

18. The method of claim 16, wherein the second end portion of the tether includes an adjustment mechanism defining an opening;
the coupling the second end portion includes:
disposing a bone screw through the opening defined by the adjustment mechanism;
advancing a portion of the bone screw into the second ilium.

19. The method of claim 16, wherein the adjusting includes moving the L5 spinous process in a cephalic direction.

20. The method of claim 16, wherein the adjusting includes applying a force to the L5 spinous process via the central portion of the tether.

21. The method of claim 16, wherein:
the second end portion of the tether includes an adjustment mechanism including a housing and an elongate member, the elongate member having an end portion and a threaded portion, the end portion of the elongate member coupled to the second end portion of the tether, the threaded portion of the elongate member disposed within an opening defined by the housing; and
the adjusting includes rotating the elongate member relative to the housing.

22. The method of claim 16, wherein:
the tension of the tether is maintained after the adjusting.

* * * * *